United States Patent
Haddach et al.

(10) Patent No.: US 6,500,839 B2
(45) Date of Patent: Dec. 31, 2002

(54) CRF RECEPTOR ANTAGONISTS AND METHODS RELATING THERETO

(75) Inventors: Mustapha Haddach, San Diego, CA (US); John Patrick Williams, San Diego, CA (US); Michael K. Schwaebe, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 22 days.

(21) Appl. No.: 09/861,194

(22) Filed: May 18, 2001

(65) Prior Publication Data
US 2002/0032196 A1 Mar. 14, 2002

Related U.S. Application Data
(60) Provisional application No. 60/205,644, filed on May 18, 2000, and provisional application No. 60/205,885, filed on May 18, 2000.

(51) Int. Cl.[7] .................. A61K 31/505; A61K 31/44; C07D 491/00; C07D 515/00
(52) U.S. Cl. .................. 514/291; 514/267; 514/292; 514/293; 544/250; 544/251; 546/80; 546/81; 546/82
(58) Field of Search .............. 514/267, 291–293; 544/250, 251; 546/80–82

(56) References Cited

U.S. PATENT DOCUMENTS 6,121,278 A * 9/2000 Jackson et al. .......... 514/222.8

FOREIGN PATENT DOCUMENTS

| WO | WO 98/08846 | 3/1998 |
|----|-------------|--------|
| WO | WO 00/27850 | 5/2000 |

* cited by examiner

Primary Examiner—Mukund J. Shah
Assistant Examiner—Tamthom N. Truong
(74) Attorney, Agent, or Firm—Seed IP Law Group PLLC

(57) ABSTRACT

CRF receptor antagonists are disclosed which have utility in the treatment of a variety of disorders, including the treatment of disorders manifesting hypersecretion of CRF in a warm-blooded animals, such as stroke. The CRF receptor antagonists of this invention have the following structure:

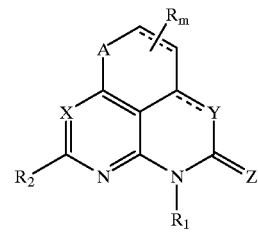

including stereoisomers, prodrugs and pharmaceutically acceptable salts thereof, wherein m, R, $R_1$, $R_2$, A, X, Y and Z are as defined herein. Compositions containing a CRF receptor antagonist in combination with a pharmaceutically acceptable carrier are also disclosed, as well as methods for use of the same.

23 Claims, No Drawings

CRF RECEPTOR ANTAGONISTS AND METHODS RELATING THERETO

CROSS-REFERENCE TO RELATED APPLICATIONS

This application claims the benefit of U.S. Provisional Application No. 60/205,644 filed May 18, 2000 and U.S. Provisional Application No. 60/205,885 filed May 18, 2000.

TECHNICAL FIELD

This invention relates generally to CRF receptor antagonists, and to methods of treating disorders by administration of such antagonists to a warm-blooded animal in need thereof.

BACKGROUND OF THE INVENTION

The first corticotropin-releasing factor (CRF) was isolated from ovine hypothalmi and identified as a 41-amino acid peptide (Vale et al., *Science* 213:1394–1397, 1981). Subsequently, sequences of human and rat CRF were isolated and determined to be identical, but different from ovine CRF in 7 of the 41 amino acid residues (Rivier et al., *Proc. Natl. Acad. Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394–1397, 1981). Briefly, CRF is believed to initiate its biological effects by binding to a plasma membrane receptor which has been found to be distributed throughout the brain (DeSouza et al., *Science* 224:1449–1451, 1984), pituitary (DeSouza et al., *Methods Enzymol.* 124:560, 1986; Wynn et al., *Biochem. Biophys. Res. Comm.* 110:602–608, 1983), adrenals (Udelsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118:1171–1179, 1986) which mediates CRF-stimulated increase in intracellular production of cAMP (Bilezikjian, L. M., and W. W. Vale, *Endocrinology* 113:657–662, 1983). The receptor for CRF has now been cloned from rat (Perrin et al., *Endo* 133(6):3058–3061, 1993), and human brain (Chen et al., *PNAS* 90(19):8967–8971, 1993; Vita et al., *FEBS* 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J. Physiol.* 255:R744, 1988). Furthermore, clinical data suggests that CRF may be hypersecreted in the brain in depression, anxiety-related disorders, and anorexia nervosa. (DeSouza, *Ann. Reports in Med. Chem.* 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyrazoline derivatives (Abreu et al., U.S. Pat. No. 5,063,245) and substituted 2-aminothiazole derivatives (Courtemanche et al., Australian Patent No. AU-A-41399/93) have been reported as CRF receptor antagonists. These particular derivatives were found to be effective in inhibiting the binding of CRF to its receptor in the 1–10 µM range and 0.1–10 µM range, respectively.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structure (I):

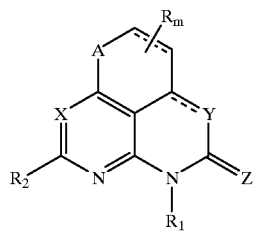

(I)

including stereoisomers, prodrugs and pharmaceutically acceptable salts thereof, wherein m, R, $R_1$, $R_2$, A, X, Y and Z are as defined below.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists.

In a first embodiment, the CRF receptor antagonists of this invention have the following structure (I):

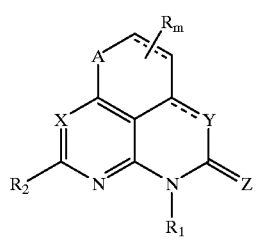

(I)

including stereoisomers, prodrugs and pharmaceutically acceptable salts thereof, wherein:

X is nitrogen or $CR_3$;

Z is O, S or $NR_4$;

Y is N, $NR_5$ or O;

A is O, S, or $NR_6$;

each occurrence of "----" represents an optional double bond;

R is an optional substituent which, at each occurrence, is independently alkyl, aryl, heteroaryl, alkylidenyl, arylalkyl or heteroarylalkyl, wherein m is 0, 1, 2 or 3 and represents the number of R substituents;

$R_1$ is alkyl, substituted alkyl, aryl, substituted aryl, heteroaryl or substituted heteroaryl;

$R_2$ is hydrogen, alkyl, substituted alkyl, alkoxy or thioalkyl;

$R_3$ is hydrogen, halogen, alkyl or substituted alkyl;

$R_4$ is hydrogen, cyano, nitro, alkyl or substituted alkyl;

$R_5$ is hydrogen, alkyl or substituted alkyl; and $R_6$ is hydrogen, alkyl, substituted alkyl, aryl, substituted aryl, heteroaryl or substituted heteroaryl.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$cyclopropyl, —$CH_2$cyclobutyl, —$CH_2$cyclopentyl, —$CH_2$cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl, Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Alkylidenyl" represents a divalent alkyl from which two hydrogen atoms are taken from the same carbon atom, such as =$CH_2$, =$CHCH_3$, =$CHCH_2CH_3$, =$C(CH_3)CH_2CH_3$, and the like.

"Aryl" means an aromatic carbocyclic moiety such as phenyl or naphthyl.

"Arylalkyl" means an alkyl having at least one alkyl hydrogen atom replaced with an aryl moiety, such as benzyl (i.e., —$CH_2$phenyl), —$CH_2$—(1 or 2-naphthyl), —($CH_2$)$_2$phenyl, —($CH_2$)$_3$phenyl, —CH(phenyl)$_2$, and the like.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The term "substituted" as used herein means any of the above groups (i.e., alkyl, aryl, arylalkyl, heteroaryl, heteroarylalkyl, heterocycle and heterocyclealkyl) wherein at least one hydrogen atom is replaced with a substituent. In the case of a keto substituent ("—C(=O)—") two hydrogen atoms are replaced. "Substituents" within the context of this invention include halogen, hydroxy, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$ —NR$_a$SO$_2$R$_b$, —OR$_a$, —C(=O)R$_a$ —C(=O)OR$_a$, —C(=O)NR$_a$R$_b$, —OC(=O) NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like. Haloalkyl is a specific embodiment of substituted alkyl, wherein alkyl is substituted with one or more halogen atoms.

"Alkoxy" means an alkyl moiety attached through an oxygen bridge (i.e., —O-alkyl) such as —O-methyl, —O-ethyl, and the like.

"Thioalkyl" means an alkyl moiety attached through a sulfur bridge (i.e., —S-alkyl) such as —S-methyl, —S-ethyl, and the like.

"Alkylamino" and "dialkylamino" mean one or two alkyl moieties attached through a nitrogen bridge (i.e., —NHalkyl or —N(alkyl)(alkyl)) such as methylamino, ethylamino, dimethylamino, diethylamino, and the like.

"Hydroxyalkyl" means an alkyl substituted with at least one hydroxyl group.

Depending upon the A, X, Y, and Z groups, representative compounds of this invention have the following structures (II) through (XII):

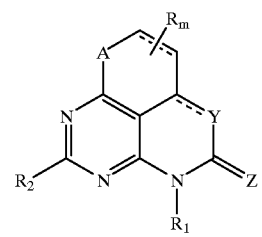

(II)

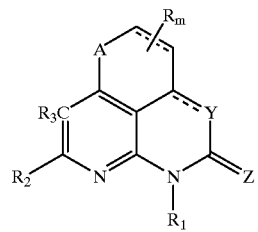

(III)

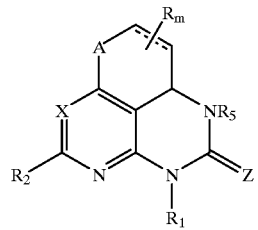

(IV)

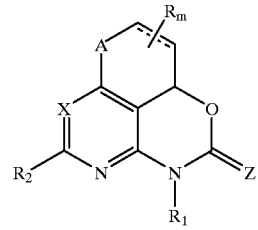

(V)

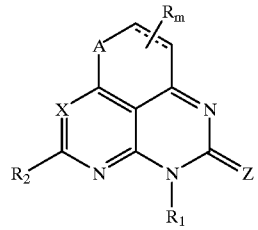

(VI)

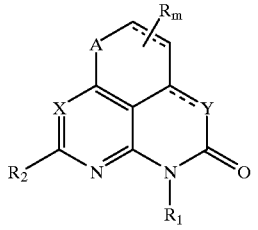

(VII)

-continued (VIII)
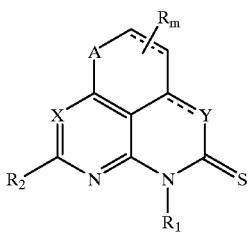

(IX)
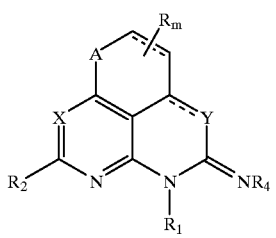

(X)
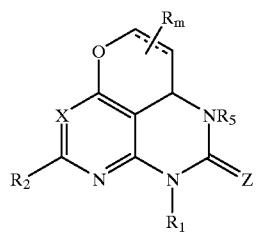

(XI)
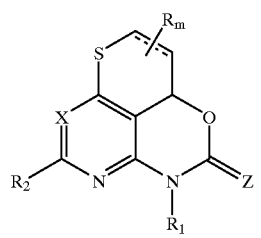

(XII)
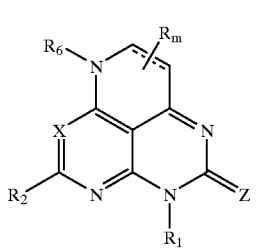

As used in the context of this invention,

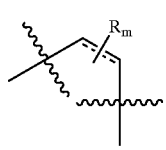

represents —CH$_2$CH$_2$— or —CH=CH— optionally substituted with 1, 2 or 3 R substituents (i.e., m=0, 1, 2 or 3). Accordingly, representative compounds of this invention also include (but are not limited to) compounds having the following structures (Ia) through (Ii), where each occurrence of R is the same or different and represents a group (other than hydrogen) as defined previously:

(Ia)
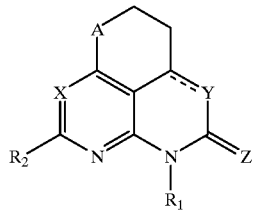

(Ib)
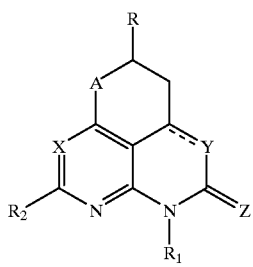

(Ic)
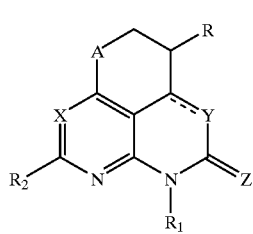

(Id)
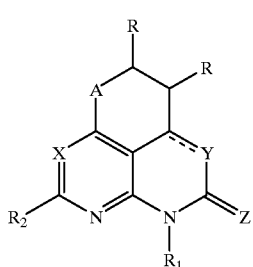

(Ie)
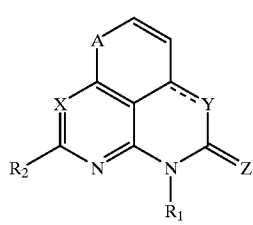

(If)
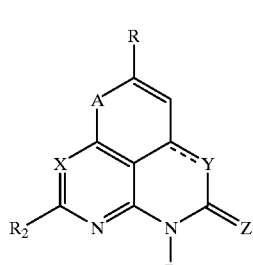

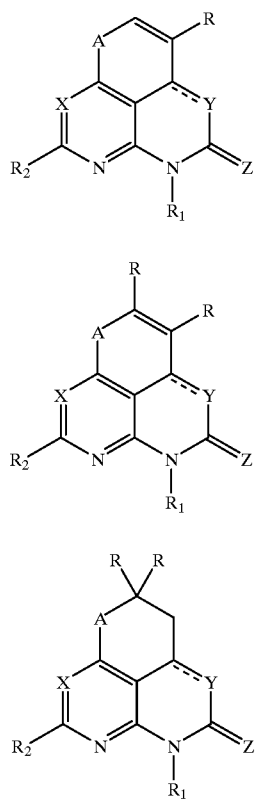

When present, representative R groups of this invention include (but are not limited to) alkyl (such as methyl, ethyl, n-propyl, isopropyl or isobutyl), aryl (such as phenyl), heteroaryl (such as pyridyl), and alkylidenyl (such as $=CH_2$ and $=CHCH_3$). In the case of R being an alkylidenyl moiety, the carbon atom to which the alkylidenyl moiety is attached must have the appropriate valency. For example, an alkylidenyl moiety would not be appropriate at the R position as shown in structure (If) above.

In more specific embodiments of this invention, representative $R_1$ groups of this invention include (but are not limited to) 2,4-dichlorophenyl, 2,4-dimethyl-phenyl, 2-chloro-4-methylphenyl, 2-methyl-4-chlorophenyl, 2,4,6-trimethylphenyl, 2-chloro-4-methoxyphenyl, 2-methyl-4-methoxyphenyl, 2,4-dimethoxyphenyl, 2-trifluoromethyl-4-chlorophenyl, 3-methoxy-4-chlorophenyl, 2,5-dimethoxy-4-chlorophenyl, 2-methoxy-4-trichloromethylphenyl, 2-methoxy-4-isopropylphenyl, 2-methoxy-4-trifluoromethylphenyl, 2-methoxy-4-isopropylphenyl 2-methoxy-4-methylphenyl, 4-methyl-6-dimethylaminopyridin-3-yl, 4-dimethylamino-6-methyl-pyridin-3-yl, 6-dimethylamino-pyridin-3-yl and 4-dimethylamino-pyridin-3-yl.

Similarly, representative $R_2$ groups include hydrogen and alkyl such as methyl and ethyl, while representative $R_3$ groups include hydrogen, halogen such as chlorine, fluorine and bromine, alkyl such as methyl and ethyl, and haloalkyl such as trifluoromethyl. Representative $R_4$ groups include alkyl such as methyl, cyano and nitro, while representative $R_5$ groups include hydrogen and methyl. Representative $R_6$ groups include alkyl such as propyl, heptyl and pentyl, and substituted alkyl where the alkyl, such as ethyl, propyl and pentyl, is substituted with groups such as alkoxy, carboxylic acid and carboxylic acid ester.

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In general, the compounds of structure (I) may be made according to the organic synthesis techniques known to those skilled in this field, as well as by the representative methods set forth in the Examples.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., [$^{125}$I] tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 μM. In a preferred embodiment of this invention, a CRF receptor antagonist has a $K_i$ of less than 1 μM, and more preferably less than 0.25 μM (i.e., 250 nM). As set forth in greater detail below, the $K_i$ values of representative compounds of this invention may be assayed by the methods set forth in Example 14.

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), pain, Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder— that is, in an amount sufficient to achieve CRF receptor antagonist activity, and preferably with acceptable toxicity to the patient. Typically, the pharmaceutical compositions of the present invention may include a CRF receptor antagonist in an amount from 0.1 mg to 250 mg per dosage depending upon the route of administration, and more commonly from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences,* Gennaro, Ed., Mack Publishing Co., Easton, Pa. 1990.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

In another embodiment, compounds of this invention and their analogs may be used as Positron Emission Tomography (PET) ligands, Single Photon Emission Computed Tomography (SPECT) ligands, or other diagnostic radiopharmaceutical agents. Incorporation of an appropriate isotope (such as $^{11}C$ or $^{18}F$ for PET or $^{125}I$ in the case of SPECT) may provide an agent useful for the diagnosis or therapeutic management of a patient. In addition, use of a compound of the present invention may provide a physiological, functional, or biological assessment of a patient or provide disease or pathology detection and assessment.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, pain, Cushing's disease, infantile spasms, epilepsy, and substance abuse or withdrawal.

The following examples are provided for purposes of illustration, not limitation.

EXAMPLES

Representative CRF receptor antagonists of this invention may be prepared as disclosed in Examples 1 through 13.

Example 14 presents a method for determining CRF receptor binding activity ($K_i$), while Example 15 is directed to an assay for screening compounds of this invention for CRF-stimulated adenylate cyclase activity.
Example 1
Synthesis of Representative Compounds
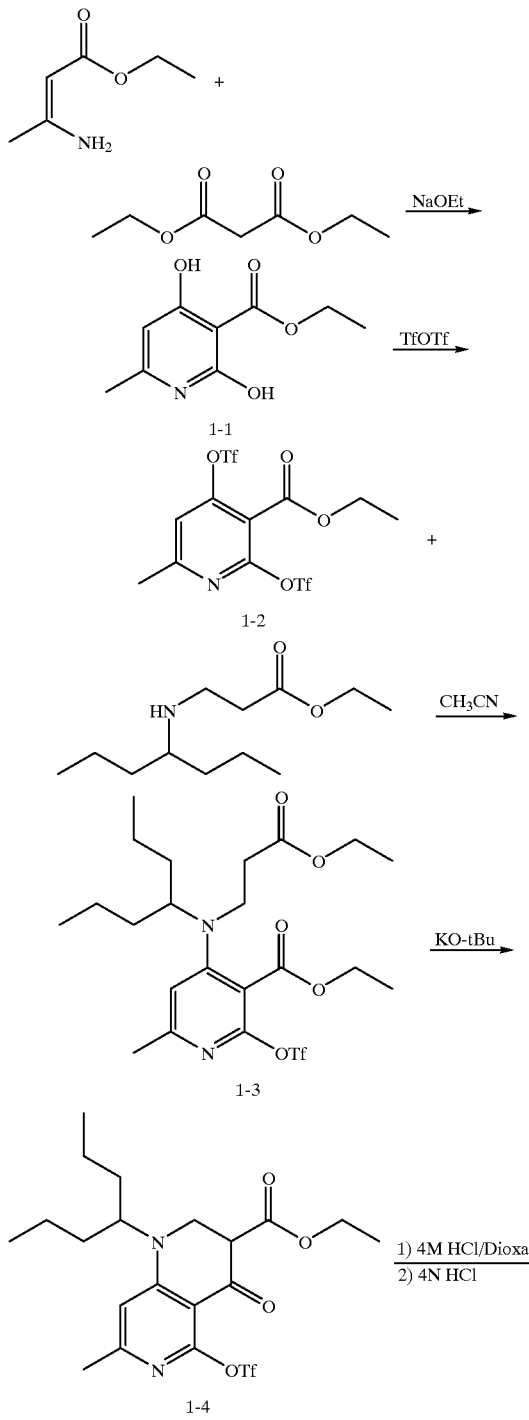
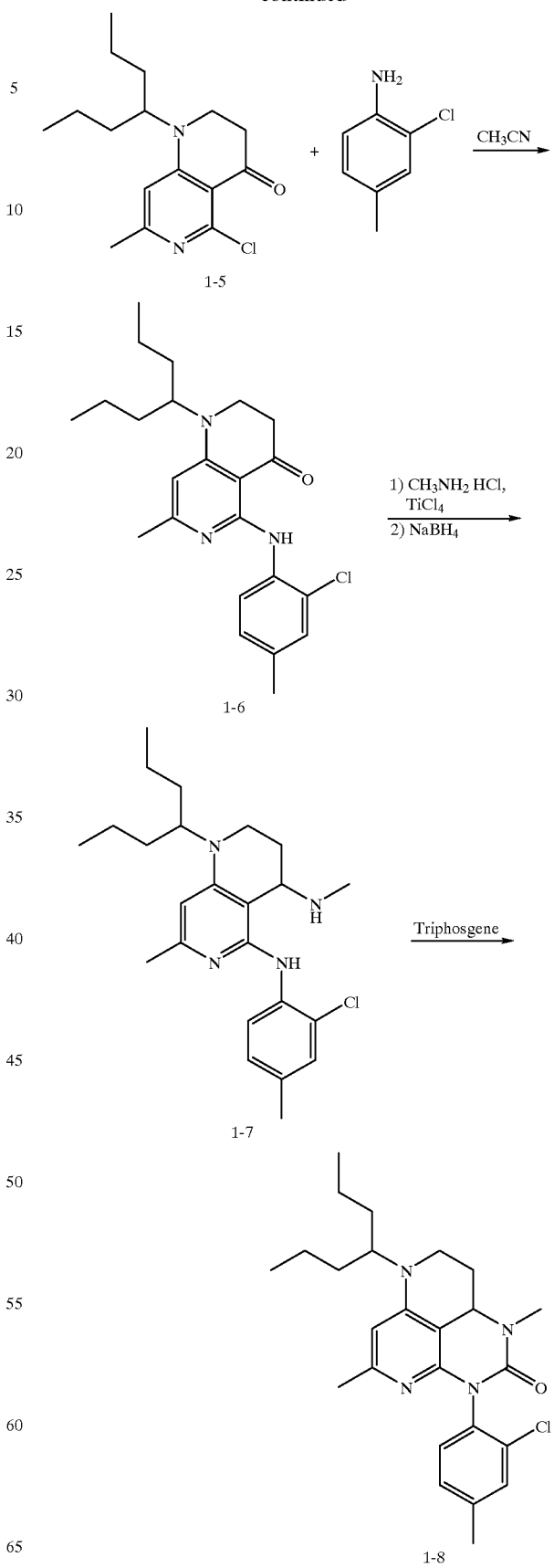

Compound 1-1

A 5 L vessel fitted with a mechanical stirrer was charged 500 mL (3.29 mol) diethyl malonate and 0.5 L diphenyl ether. To this mixture was added sodium ethoxide (224.1 g, 3.29 mol) at room temperature. The mixture was heated to 175° C. and the liberated ethanol was removed via a stream of nitrogen gas. After 30 min 416 mL ethyl-3-aminocrotonate (3.29 mol) was added, removing additional ethanol with a stream of nitrogen. After 30 minutes the mechanical stirrer could no longer stir the foamy mass. The reaction flask was cooled to room temperature and methyl-tert-butyl ether (MTBE) (1 L) was added while crushing the granular solid. The solid was filtered and washed with MTBE. The solid was then added to conc. HCl (200 mL) to solubilize the mixture. The mixture was then taken up in 500 mL chloroform (3×), and dried over sodium sulfate. The mixture was concentrated in vacuo to afford an orange gummy mass which was triturated with ether and filtered, washing again with ether. The resulting solid was recrystalized from ethanol to afford the dihydroxy pyridine ester 1-1 as pinkish needles. (253.5 g, 39%). $^1$H NMR (CDCl$_3$) δ: 5.84 (s, 1H), 4.43 (q, 2H), 2.31 (s, 3H), 1.43 (t, 3H).

Compound 1-2

To a 3 L roundbottom flask charged with pyridine-dione ester 1-1 (320 g, 1.617 mol) and triethylamine (490 mL, 3.5 mol) in 1 L methylene chloride was added triflic anhydride (950 g, 3.369 mol, diluted with 0.5 L CH$_2$Cl$_2$) at 0° C. via addition funnel over 2 hours. The mixture was allowed to warm to room temperature and was stirred for an additional 2 hours. The reaction was quenched with water (0.5 L) and the organic layer was washed with 1 N HCl (2×200 mL), brine (100 mL), dried over magnesium sulfate and filtered over a pad of silica gel (80×120 mm) eluting with ethyl ether. The solvent was removed in vacuo to afford the bis-triflate 1-2 as an oil (789.6 g) GCMS T$_r$=4.97 min., MS (70 eV, EI) m/z 461 (2), 433 (35), 416 (40), 284 (75).

Compound 1-3

To a mixture of the bis-triflate 1-2 (105.3 g, 228.4 mmol) and triethylamine (48 mL, 176.8 mmol) in acetonitrile (300 mL) at 0° C. via addition funnel over 2 hours. The mixture was allowed to warm to room temperature and stir for an additional 2 hours. The reaction mixture was then diluted with methylene chloride (500 mL) and washed with 1 N HCl (2×100 mL), brine (100 mL), dried over magnesium sulfate and filtered over a pad of silica gel (50×80 mm) eluting with ethyl ether. The solvent was removed in vacuo and the resulting material was chromatographed on silica gel eluting with ethyl acetate/hexanes 1:3 (R$_f$=0.25). The solvent was removed in vacuo to afford the 4-amino pyridine 1-3 as a colorless oil (75.3 g, 176.8 mmol, 77%). GCMS T$_r$=7.56 min., MS (70 eV, EI) m/z 497 [M−29] (2), 483 (100), 439 (5).

Compound 1-4

To a solution of the 4-amino pyridine 1-3 (75.3 g, 176.8 mmol) in ethyl ether (500 mL) at room temperature was added potassium tert-butoxide (20.8 g, 185.6 mmol) and the mixture was allowed to stir for 1 hour. The mixture was filtered to remove any hydrolyzed material. The solvent was removed in vacuo to afford the potassium salt of the bicyclic ester 1-4 as a bright yellow solid (56.1 g). MS (M+1) 481.

Compound 1-5

The bicyclic ester 1-4 (56.1 g) was dissolved in 4M HCl in dioxane (100 mL) and allowed to stir for 2 hours at room temperature. Then 4 N HCl was added and the mixture was heated on a 100° C. oil bath for 12 hours. The mixture was then cooled to room temperature and neutralized with 1N NaOH. The aqueous layer was extracted with ethyl acetate (4×100 mL), dried over magnesium sulfate and filtered over a pad of silica gel (50×80 mm) eluting with ethyl ether. The solvent was removed in vacuo to afford the chloroketone 1-5 as an oil that solidified over 2 days (24 g). GCMS T$_r$=8.15 min., MS (70 eV, EI) m/z 294 (7), 251 (100), 223 (17).

Compound 1-6

To the chloroketone 1-5 (1.98 g, 6.73 mmol) dissolved in acetonitrile was added 2-chloro-4-methyl aniline and the mixture was heated on a 80° C. oil bath for 4 hours. The solvent was then removed in vacuo to afford the 2-anilino pyridine 1-6 as an oil with ca 5% remaining aniline impurity (3.29 g). GCMS T$_r$=12.09 min., MS (70 eV, EI) m/z 399 (4), 364 (100), 292 (10), 266 (30). MS (M +1) 400.

Compound 1-7

To a mixture of the bicyclic 2-anilino pyridine 1-6 (3.29 g, 8.25 mmol), triethyl amine (11.5 mL, 82.5 mmol) and methylamine hydrochloride (2.78 g, 41.25 mmol) in methylene chloride at 0° C. was added dropwise titanium tetrachloride (16.5 mL, [1.0 M] in CH$_2$Cl$_2$). The mixture was then allowed to come to room temperature and stir under an inert atmosphere for 12 hours. The reaction was then quenched with 1N NaOH at 0° C., extracted with methylene chloride, dried over magnesium sulfate, filtered over silica gel and concentrated in vacuo. The resulting red oil was then taken up in methanol and sodium borohydride was added portionwise (large excess) until tlc analysis indicated a complete reaction. The reaction was then quenched with 1N NaOH, extracted with methylene chloride, dried over magnesium sulfate, filtered over silica gel and concentrated in vacuo to afford the methyl amino compound 1-7 as a dark oil (2.54 g). MS (M+1) 415.

Compound 1-8

To the methyl amino compound 1-7 (15 mg, 0.036 mmol) and triethyl amine (0.072 mmol) in methylene chloride at 0° C. was added triphosgene (0.036 mmol) and the reaction mixture was allowed to stir for 30 minutes. The reaction mixture was then purified on silica gel eluting with ethyl acetate/hexanes 1:3 (R$_f$=0.10). The solvent was removed in vacuo to afford the cyclic urea 1-8 as a white solid (5 mg). MS (M+1) 441.

Example 2

Synthesis of Representative Compounds

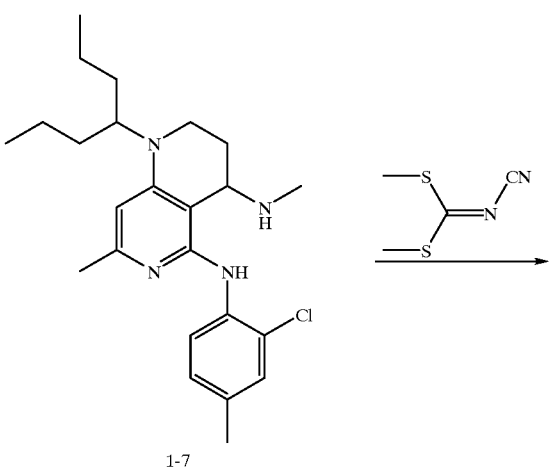

1-7

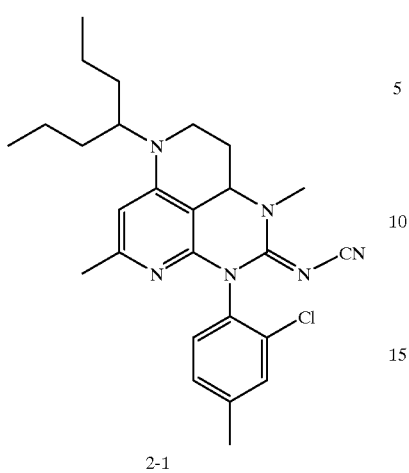

2-1

Compound 2-1

To the methyl amino compound 1-7 (from Example 1, 15 mg, 0.036 mmol) in absolute ethanol at room temperature was added dimethyl cyanodithioiminocarbonate (0.072 mmol). The reaction was heated on an 80° C. hotplate in a sealed vessel for 72 hours. The reaction mixture was then purified on silica gel eluting with ethyl acetate/hexanes 1:3 ($R_f$=0.10). The solvent was removed in vacuo to afford the N-cyanoguanidine 2-1 as a white solid (5 mg). MS (M+1) 465.

Example 3

Synthesis of Representative Compounds

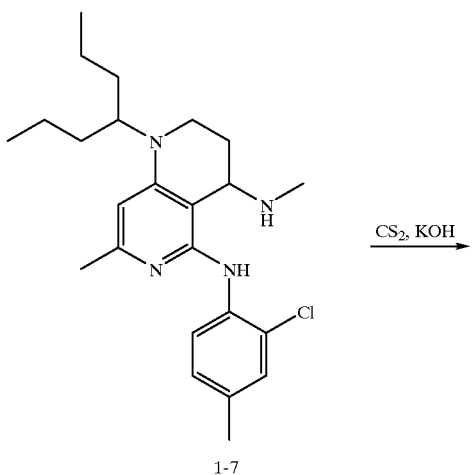

1-7

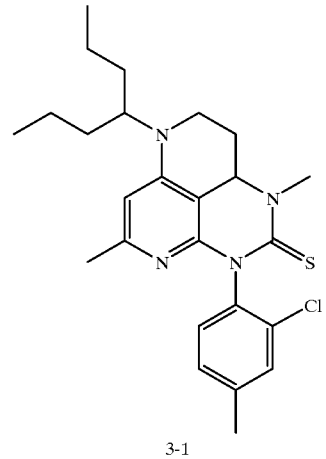

3-1

Compound 3-1

To the methyl amino compound 1-7 (from Example 1, 50 mg, 0.12 mmol) dissolved in ethanol was added 4N KOH (0.1 mL, 0.40 mmol) and carbon disulfide (1.5 mmol). The reaction mixture was heated on a 60° C. plate for 12 hours. The solvent was removed in vacuo and replaced with ethyl acetate, washing with brine. The organic layer was dried over magnesium sulfate and the product was then purified on silica gel eluting with ethyl acetate/hexanes 1:3 ($R_f$=0.45). The solvent was removed in vacuo to afford the cyclic thiourea 3-1 as a white solid (25 mg). MS (M+1) 457.

Example 4

Synthesis of Representative Compounds

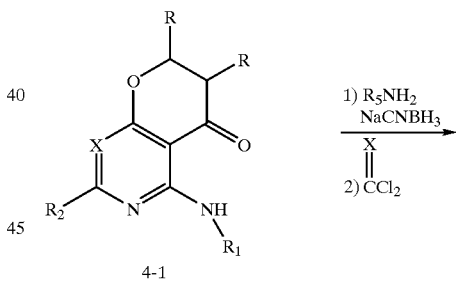

4-1

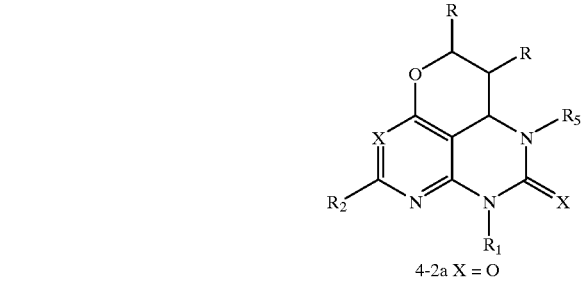

4-2a X = O
4-2b X = S

Compound 4-2

Compound 4-1 (0.095 mmol) and $R_5NH_2$ (0.20 mL) are dissolved in acetonitrile (1 mL) and treated with sodium cyanoborohydride (25 mg). Acetic acid (1 drop) is added and the mixture is stirred for 4 hours, diluted with aq. $NaHCO_3$ (2 mL), and extracted with ethyl acetate (4×2 mL). The combined organic extracts are dried (MgSO$_4$), concentrated under vacuum, and the residue is taken up in toluene (1 mL) and treated with a solution of phosgene in toluene (20%, 0.1 mL). After 18 hours, the solution is concentrated under vacuum and the residue is purified by preparative TLC to afford urea 4-2a. Similar treatment of the intermediate amine adduct with thiophosgene produces the thiourea 4-2b.

Example 5

Synthesis of Representative Intermediate

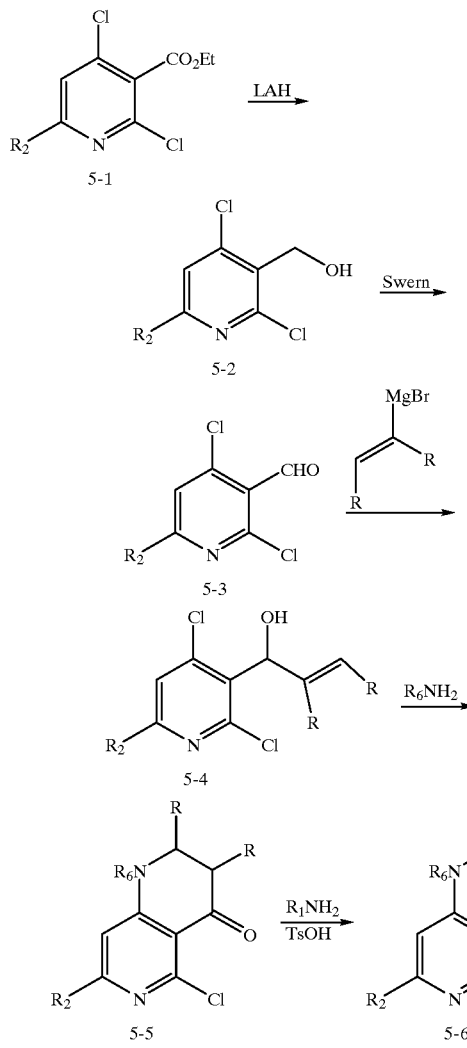

Compound 5-2

Chloropyridine 5-1 is dissolved in THF and added to a stirred suspension of LAH in THF at −78° C. The mixture is stirred for 6 hours at this temperature and for 1 hour at −30° C. The mixture is then treated cautiously with water, 15% aqueous NaOH and water with vigorous stirring. The mixture is warmed to room temperature and filtered. The white precipitate is washed liberally with ethyl acetate. The combined organic portions are dried (MgSO$_4$) and concentrated under vacuum. Purification via flash chromatography gives the desired 5-2.

Compound 5-3

DMSO (6 equivalents) is added to a stirred solution of oxalyl chloride (3 equivalents) in dichloromethane at −70° C. After 15 min, alcohol 5-2 (1 equivalent) in dichloromethane is added, followed by triethylamine. The mixture is allowed to warm to room temperature and stirred for 1 hour. The mixture is washed with aqueous sodium bicarbonate (75 mL), dried (MgSO$_4$), and concentrated under vacuum. Purification via flash chromatography gives the desired product 5-3.

Compound 5-4

Alkenylmagnesium bromide in THF (1equivalent) is added to a stirred solution of aldehyde 5-3 (1equivalent) in THF at −78° C. The mixture is stirred at this temperature for 30 minutes, warmed to room temperature and quenched with aqueous sodium bicarbonate The mixture is then extracted with ethyl acetate and the combined extracts are dried (MgSO$_4$) and concentrated under vacuum. Purification via flash chromatography gives the desired 5-4.

Compound 5-5

Compound 5-4 and R$_6$NH$_2$ (1 equivalent) in ethanol (20 mL) are heated at 60° C. for 16 hours. The mixture is concentrated, taken up in ethyl acetate (50 mL), washed with aq. NaHCO$_3$ (20 mL), dried (MgSO$_4$) and concentrated under vacuum. The residue is purified on a silica gel column (elution with 25% ethyl acetate in hexanes) to afford 5-5.

Compound 5-6

Ketone 5-5 (0.16 mmol), toluenesulfonic acid monohydrate (30 mg, 0.16 mmol) and R$_1$NH$_2$ (0.18 mmol) are dissolved in ethanol (0.5 mL) and heated at 80° C. in a sealed tube for 20 hours. The mixture is cooled to room temperature, diluted with aq. NaHCO$_3$ (2 mL), and extracted with ethyl acetate (4×2 mL). The combined organic extracts are dried (MgSO$_4$), concentrated under vacuum, and the residue is purified by preparative TLC to afford 5-6.

Example 6

Synthesis of Representative Intermediate

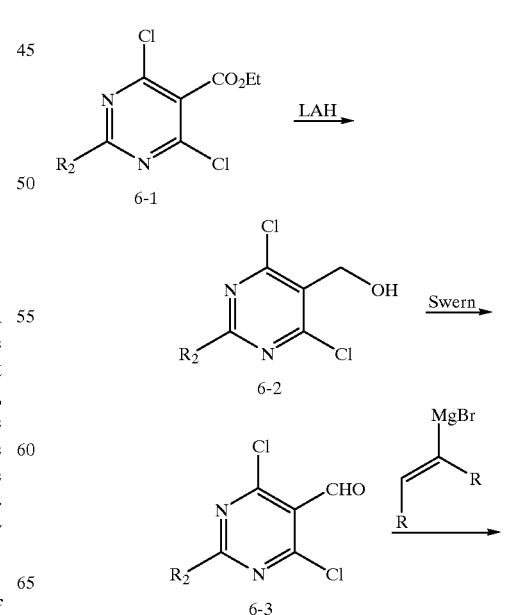

-continued

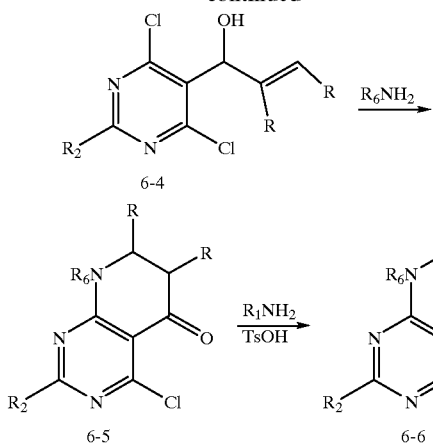

Compound 6-2

The chloropyrimidine 6-1 is dissolved in THF and added to a stirred suspension of LAH in THF at −78° C. The mixture is stirred for 6 hours at this temperature and for 1 hour at −30° C. The mixture is then treated cautiously with water, 15% aqueous NaOH and water with vigorous stirring. The mixture is warmed to room temperature and filtered. The white precipitate is washed liberally with ethyl acetate. The combined organic portions are dried (MgSO$_4$) and concentrated under vacuum. Purification via flash chromatography gives the desired product 6-2.

Compound 6-3

DMSO (6 equivalents) is added to a stirred solution of oxalyl chloride (3 equivalents) in dichloromethane at −70° C. After 15 min, alcohol 6-2 (1 equivalent) in dichloromethane is added, followed by triethylamine. The mixture is allowed to warm to room temperature and stirred for 1 hour. The mixture is washed with aqueous sodium bicarbonate (75 mL), dried (MgSO$_4$), and concentrated under vacuum. Purification via flash chromatography gives the desired product 6-3.

Compound 6-4

Alkenylmagnesium bromide in THF (1 equivalent) is added to a stirred solution of aldehyde 6-3 (1 equivalent) in THF at −78° C. The mixture is stirred at this temperature for 30 minutes, warmed to room temperature and quenched with aqueous sodium bicarbonate. The mixture is extracted with ethyl acetate and the combined extracts are dried (MgSO$_4$) and concentrated under vacuum. Purification via flash chromatography gives the desired product 6-4.

Compound 6-5

Compound 6-4 and R$_6$NH$_2$ (1 equivalent) in ethanol (20 mL) are heated at 60° C. for 16 hours. The mixture is concentrated, taken up in ethyl acetate (50 mL), washed with aq. NaHCO$_3$ (20 mL), dried (MgSO$_4$) and concentrated under vacuum. The residue is purified on a silica gel column (elution with 25% ethyl acetate in hexanes) to afford 6-5.

Compound 6-6

Ketone 6-5 (0.16 mmol), toluenesulfonic acid monohydrate (30 mg, 0.16 mmol) and R$_1$NH$_2$ (0.18 mmol) are dissolved in ethanol (0.5 mL) and heated at 80° C. in a sealed tube for 20 hours. The mixture is cooled to room temperature, diluted with aq. NaHCO$_3$ (2 mL), and extracted with ethyl acetate (4×2 mL). The combined organic extracts are dried (MgSO$_4$), concentrated under vacuum, and the residue is purified by preparative TLC to afford 6-6.

Example 7

Synthesis of Representative Compounds

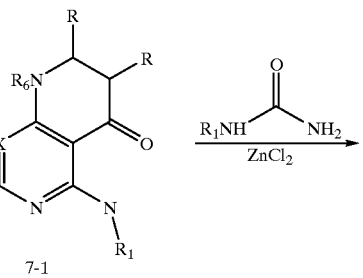

Compound 7-2

Ketone 7-1 (0.16 mmol), urea (30 mg) and ZnCl$_2$ (25 mg) are heated at 200° C. for 5 hours. The mixture is cooled to room temperature, diluted with aq. NaHCO$_3$ (2 mL), and extracted with ethyl acetate (4×2 mL). The combined organic extracts are dried (MgSO$_4$), concentrated under vacuum, and the residue is purified by preparative TLC to afford urea 7.

Compound 7-3

The urea 7 (0.070 mmol) and PCl$_5$ (15 mg, 0.070 mmol) are heated in toluene at 90° C. for 3 hours during which time a white solid forms. The mixture is cooled to room temperature and treated with R$_4$NH$_2$ (0.10 mL). Stirring is continued for 30 min. The mixture is diluted with aq. NaHCO$_3$ (2 mL), and extracted with ethyl acetate (4×2 mL). The combined organic extracts are dried (MgSO$_4$), concentrated under vacuum, and the residue is purified by preparative TLC to afford guanidine 8.

Example 8

Synthesis of Representative Compounds

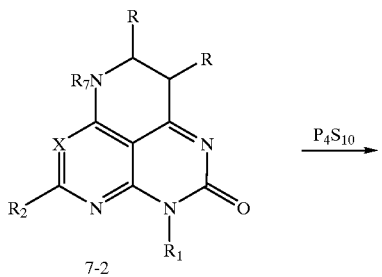

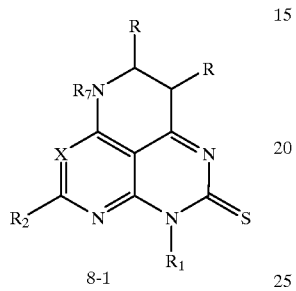

Compound 8-1

Urea 7-2 (from Example 7, 0.070 mmol) and $P_4S_{10}$ (50 mg) are heated in toluene at 90° C. for 20 hours. The mixture is cooled to room temperature, diluted with aq. $NaHCO_3$ (2 mL), and extracted with ethyl acetate (4×2 mL). The combined organic extracts are dried ($MgSO_4$), concentrated under vacuum, and the residue is purified by preparative TLC to afford thiourea 8-1.

Example 9

Synthesis of Representative Compounds

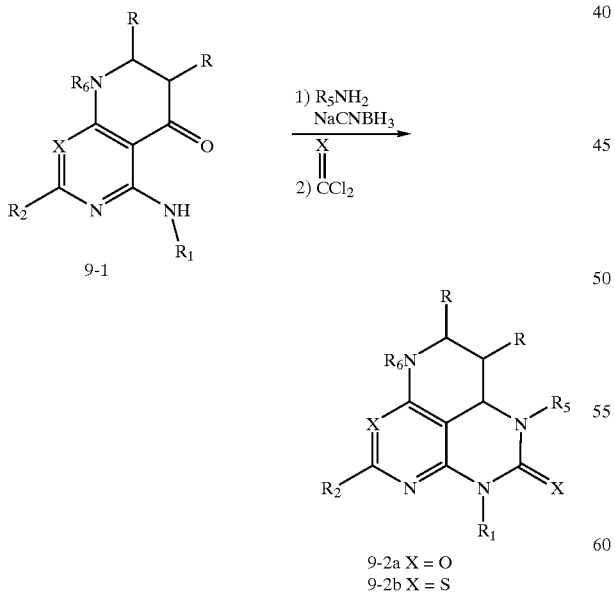

Compound 9-2

Compound 9-1 (0.095 mmol) and $R_5NH_2$ (0.20 mL) are dissolved in acetonitrile (1 mL) and treated with sodium cyanoborohydride (25 mg). Acetic acid (1 drop) is added and the mixture is stirred for 4 hours, diluted with aq. $NaHCO_3$ (2 mL), and extracted with ethyl acetate (4×2 mL). The combined organic extracts are dried ($MgSO_4$), concentrated under vacuum, and the residue is taken up in toluene (1 mL) and treated with a solution of phosgene in toluene (20%, 0.1 mL). After 18 hours, the solution is concentrated under vacuum and the residue is purified by preparative TLC to afford urea 9-2a. Similar treatment of the intermediate amine adduct with thiophosgene produces the thiourea 9-2b.

Example 10

Synthesis of Representative Intermediate

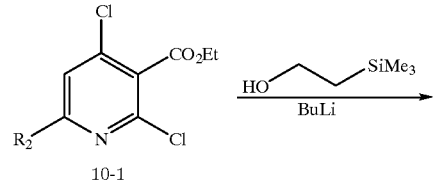

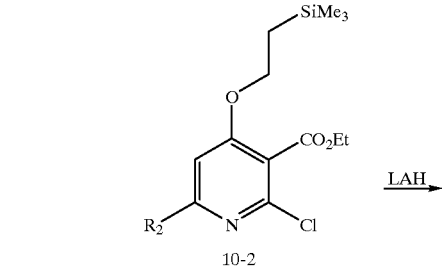

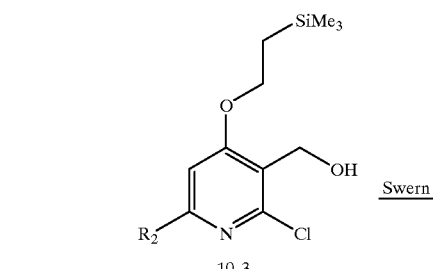

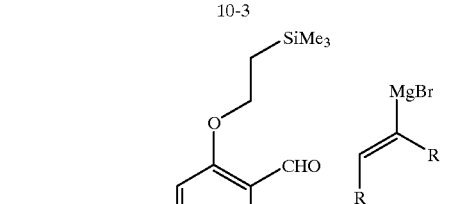

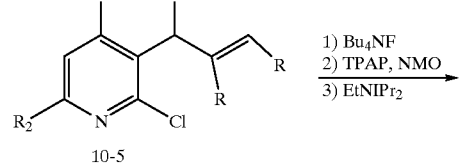

-continued

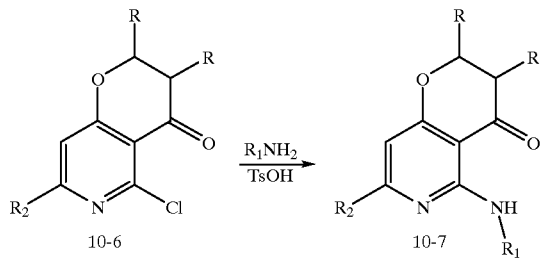

Compound 10-2

Trimethylsilylethanol is treated with n-butyllithium at −78° C. in THF. After 15 minutes dichloropyridine 10-1 is added and the mixture is allowed to warm to room temperature. The mixture is then heated at 50° C. for 2 hours. Upon cooling to room temperature the mixture is poured into saturated $NH_4Cl$ and extracted with ethyl acetate. The organic layers are combined and washed three times with water and brine. The organic phase is dried ($MgSO_4$) and concentrated in vacuo. Purification via flash chromatography gives the desired product 10-2.

Compound 10-3

Chloropyridine 10-2 is dissolved in THF and added to a stirred suspension of LAH in THF at −78° C. The mixture is stirred for 6 hours at this temperature and for 1 hour at −30° C. The mixture is then treated cautiously with water, 15% aqueous NaOH and water with vigorous stirring. The mixture is warmed to room temperature and filtered. The white precipitate is washed liberally with ethyl acetate. The combined organic portions are dried ($MgSO_4$) and concentrated under vacuum. Purification via flash chromatography gives the desired product 10-3.

Compound 10-4

DMSO (6 equivalents) is added to a stirred solution of oxalyl chloride (3 equivalents) in dichloromethane at −70° C. After 15 min, alcohol 10-3 (1 equivalent) in dichloromethane is added, followed by triethylamine. The mixture is allowed to warm to room temperature and stirred for 1 hour. The mixture is washed with aqueous sodium bicarbonate (75 mL), dried ($MgSO_4$), and concentrated under vacuum. Purification via flash chromatography gives the desired product 10-4.

Compound 10-5

Alkenylmagnesium bromide in THF (1 equivalent) is added to a stirred solution of aldehyde 10-4 (1equivalent) in THF at −78° C. The mixture is stirred at this temperature for 30 minutes, warmed to room temperature and quenched with aqueous sodium bicarbonate. The mixture is then extracted with ethyl acetate and the combined extracts are dried ($MgSO_4$) and concentrated under vacuum. Purification via flash chromatography gives the desired product 10-5.

Compound 10-6

The allylic alcohol 10-5 is treated with tetrabutylammonium fluoride in THF. After 1 hour the mixture is diluted with ethyl acetate and washed with saturated ammonium chloride, dried ($MgSO_4$) and concentrated in vacuo. The crude mixture and N-methylmorpholine N-oxide (1.5 equivalents) are dissolved in dichloromethane and stirred in the presence of 4 angstrom molecular sieves for 20 minutes. Catalytic tetrapropylammonium perruthenate is added and the mixture is stirred for 1 hour. The mixture is filtered (Celite) and concentrated under vacuum. The crude mixture is dissolved in 5 equivalents of diisopropylethylamine and heated at 50° C. for 6 hours. The resultant mixture is concentrated in vacuo and purification via flash chromatography provides the desired product 10-6.

Compound 10-7

Ketone 10-6 (0.16 mmol), toluenesulfonic acid monohydrate (30 mg, 0.16 mmol) and $R_1NH_2$ (0.18 mmol) are dissolved in ethanol (0.5 mL) and heated at 80° C. in a sealed tube for 20 hours. The mixture is cooled to room temperature, diluted with aq. $NaHCO_3$ (2 mL), and extracted with ethyl acetate (4×2 mL). The combined organic extracts are dried ($MgSO_4$), concentrated under vacuum, and the residue is purified by preparative TLC to afford 10-7.

Example 11

Synthesis of Representative Intermediate

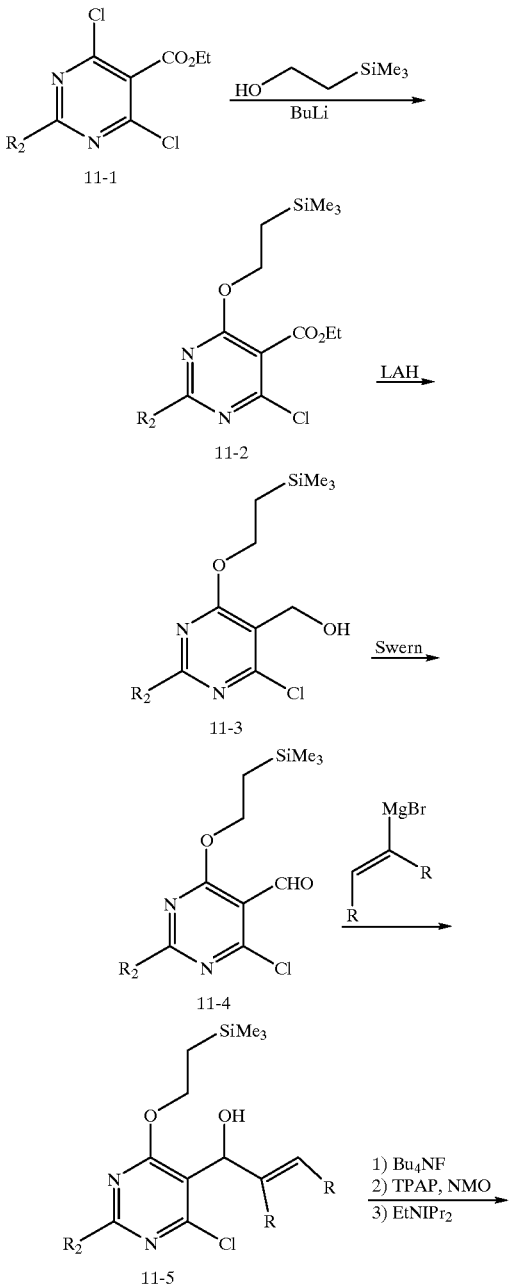

-continued

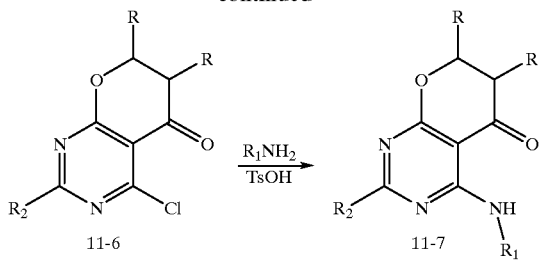

Compound 11-2

Trimethylsilylethanol is treated with n-butyllithium at −78° C. in THF. After 15 minutes, dichloropyrimidine 11-1 is added and the mixture is allowed to warm to room temperature. The mixture is then heated at 50° C. for 2 hours. Upon cooling to room temperature the mixture is poured into saturated $NH_4Cl$ and extracted with ethyl acetate. The organic layers are combined and washed three times with water and brine. The organic phase is dried ($MgSO_4$) and concentrated in vacuo. Purification via flash chromatography gives the desired product 11-2.

Compound 11-3

The chloropyrimidine 11-2 is dissolved in THF and added to a stirred suspension of LAH in THF at −78° C. The mixture is stirred for 6 hours at this temperature and for 1 hour at −30° C. The mixture is then treated cautiously with water, 15% aqueous NaOH and water with vigorous stirring. The mixture is warmed to room temperature and filtered. The white precipitate is washed liberally with ethyl acetate. The combined organic portions are dried ($MgSO_4$) and concentrated under vacuum. Purification via flash chromatography gives the desired product 11-3.

Compound 11-4

DMSO (6 equivalents) is added to a stirred solution of oxalyl chloride (3 equivalents) in dichloromethane at −70° C. After 15 min, alcohol 11-3 (1 equivalent) in dichloromethane is added, followed by triethylamine. The mixture is allowed to warm to room temperature and stirred for 1 hour. The mixture is washed with aqueous sodium bicarbonate (75 mL), dried ($MgSO_4$), and concentrated under vacuum. Purification via flash chromatography gives the desired product 11-4.

Compound 11-5

Alkenylmagnesium bromide in THF (1 equivalent) is added to a stirred solution of aldehyde 11-4 (1 equivalent) in THF at −78° C. The mixture is stirred at this temperature for 30 minutes, warmed to room temperature and quenched with aqueous sodium bicarbonate The mixture is extracted with ethyl acetate and the combined extracts are dried ($MgSO_4$) and concentrated under vacuum. Purification via flash chromatography gives the desired product 11-5.

Compound 11-6

The allylic alcohol 11-5 is treated with tetrabutylammonium fluoride in THF. After 1 hour the mixture is diluted with ethyl acetate and washed with saturated ammonium chloride, dried ($MgSO_4$) and concentrated in vacuo. The crude mixture and N-methylmorphine N-oxide (1.5 equivalents) are dissolved in dichloromethane and stirred in the presence of 4 angstrom molecular sieves for 20 minutes. Catalytic tetrapropylammonium perruthenate is added and the mixture stirred for 1 hour. The mixture is filtered (Celite) and concentrated under vacuum. The crude mixture is dissolved in 5 equivalents of diisopropylethylamine and heated at 50° C. for 6 hours. The resultant mixture is concentrated in vacuo and purification via flash chromatography provides the desired product 11-6.

Compound 11-7

Ketone 11-6 (0.16 mmol), toluenesulfonic acid monohydrate (30 mg, 0.16 mmol) and $R_1NH_2$ (0.18 mmol) are dissolved in ethanol (0.5 mL) and heated at 80° C. in a sealed tube for 20 hours. The mixture is cooled to room temperature, diluted with aq. $NaHCO_3$ (2 mL), and extracted with ethyl acetate (4×2 mL). The combined organic extracts are dried ($MgSO_4$), concentrated under vacuum, and the residue is purified by preparative TLC to afford 11-7.

Example 12

Synthesis of Representative Compounds

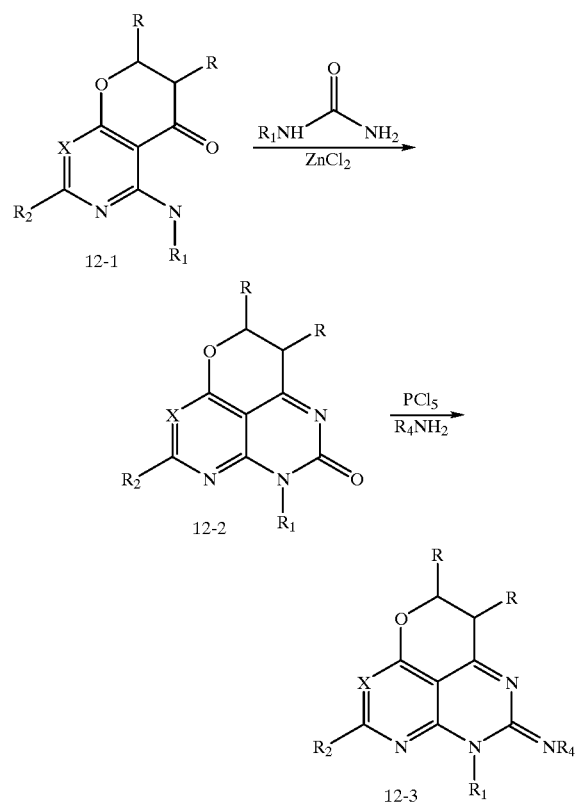

Compound 12-2

Ketone 12-1 (0.16 mmol), urea (30 mg) and $ZnCl_2$ (25 mg) are heated at 200° C. for 5 hours. The mixture is cooled to room temperature, diluted with aq. $NaHCO_3$ (2 mL), and extracted with ethyl acetate (4×2 mL). The combined organic extracts are dried ($MgSO_4$), concentrated under vacuum, and the residue is purified by preparative TLC to afford urea 12-2.

Compound 12-3

The urea 12-2 (0.070 mmol) and $PCl_5$ (15 mg, 0.070 mmol) are heated in toluene at 90° C. for 3 hours during which time a white solid forms. The mixture is cooled to room temperature and treated with $R_4NH_2$ (0.10 mL). Stirring is continued for 30 min. The mixture is diluted with aq. $NaHCO_3$ (2 mL), and extracted with ethyl acetate (4×2 mL). The combined organic extracts are dried ($MgSO_4$), concentrated under vacuum, and the residue is purified by preparative TLC to afford guanidine 12-3.

Example 13

Synthesis of Representative Compounds

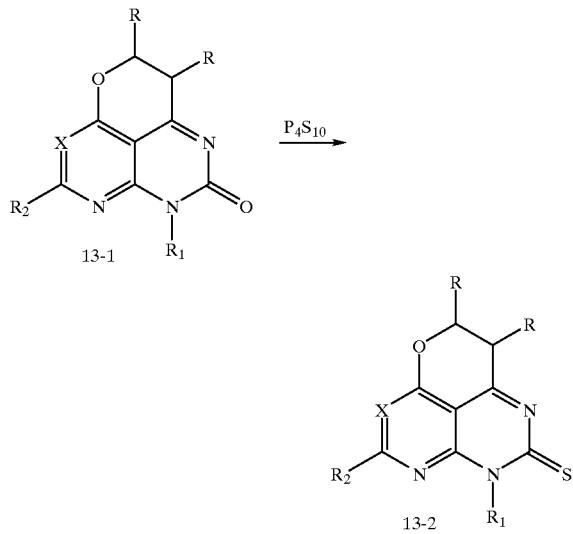

Compound 13-2

Urea 13-1 (0.070 mmol) and $P_4S_{10}$ (50 mg) are heated in toluene at 90° C. for 20 hours. The mixture is cooled to room temperature, diluted with aq. $NaHCO_3$ (2 mL), and extracted with ethyl acetate (4×2 mL). The combined organic extracts are dried ($MgSO_4$), concentrated under vacuum, and the residue is purified by preparative TLC to afford thiourea 13-2.

Example 14

CRF Receptor Binding Activity

The compounds of this invention may be evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 mL Eppendorf tubes using approximately $1×10^6$ cells per tube stably transfected with human CRF receptors. Each tube receives about 0.1 mL of assay buffer (e.g., Dulbecco's phosphate buffered saline, 10 mM magnesium chloride, 20 $\mu M$ bacitracin) with or without unlabeled sauvagine, urotensin I or CRF (final concentration, 1 $\mu M$) to determine nonspecific binding, 0.1 ml of [$^{125}$I] tyrosine—ovine CRF (final concentration ~200 pM or approximately the $K_D$ as determined by Scatchard analysis) and 0.1 mL of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the non-linear least-square curve-fitting program LIGAND of Munson and Rodbard (*Anal. Biochem.* 107:220, 1990).

Example 15

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 mL: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 $\mu l$ of a solution of 95% ethanol and 20 mM aqueous hydrochloric acid is added to each well and the resulting suspensions are incubated at −20° C. for 16 to 18 hours. The solution is removed into 1.5 mL Eppendorf tubes and the wells washed with an additional 200 $\mu l$ of ethanol/aqueous hydrochloric acid and pooled with the first fraction. The samples are lyophilized and then resuspended with 500 $\mu l$ sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds ($10^{-12}$ to $10^{-6}$ M).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound having the following structure:
the following structure (I):

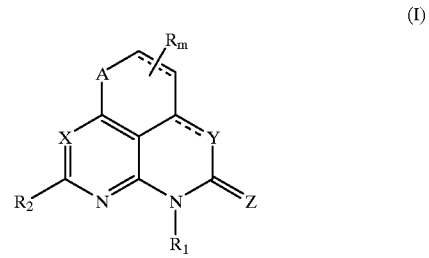

or a stereoisomer, prodrug or pharmaceutically acceptable salt thereof,
  wherein:
    X is nitrogen or $CR_3$;
    Z is O, S or $NR_4$;
    Y is N, $NR_5$ or O;
    A is O, S, or $NR_6$;
    "----" represents an optional double bond;
    R is an optional substituent which, at each occurrence, is independently alkyl, aryl, heteroaryl, alkylidenyl, arylalkyl or heteroarylalkyl, wherein m is 0, 1, 2 or 3 and represents the number of R substituents;

$R_1$ is alkyl, substituted alkyl, aryl, substituted aryl, heteroaryl or substituted heteroaryl;

$R_2$ is hydrogen, alkyl, substituted alkyl, alkoxy or thioalkyl;

$R_3$ is hydrogen, halogen, alkyl or substituted alkyl;

$R_4$ is hydrogen, cyano, nitro, alkyl or substituted alkyl;

$R_5$ is hydrogen, alkyl or substituted alkyl; and $R_6$ is hydrogen, alkyl, substituted alkyl, aryl, substituted aryl, heteroaryl or substituted heteroaryl.

2. The compound of claim 1 wherein X is $CR_3$.
3. The compound of claim 1 wherein X is nitrogen.
4. The compound of claim 1 wherein A is O.
5. The compound of claim 1 wherein A is S.
6. The compound of claim 1 wherein A is $NR_6$.
7. The compound of claim 6 wherein $R_6$ is alkyl.
8. The compound of claim 1 wherein Y is N.
9. The compound of claim 1 wherein Y is $NR_5$.
10. The compound of claim 9 wherein $R_5$ is alkyl.
11. The compound of claim 1 wherein Y is O.
12. The compound of claim 1 wherein Z is O.
13. The compound of claim 1 wherein Z is S.
14. The compound of claim 1 wherein Z is $NR_4$.
15. The compound of claim 1 wherein $R_1$ is substituted aryl.
16. The compound of claim 15 wherein $R_1$ is substituted phenyl.
17. The compound of claim 1 wherein $R_2$ is alkyl.
18. The compound of claim 1 wherein m is O.
19. A composition comprising a compound of claim 1 in combination with a pharmaceutically acceptable carrier or diluent.
20. A method for treating a disorder manifesting hypersecretion of CRF in a warm-blooded animal, comprising administering to the animal an effective amount of the composition of claim 19.
21. The method of claim 20 wherein the disorder is stroke.
22. The method of claim 20 wherein the disorder is depression.
23. The method of claim 20 wherein the disorder is anxiety.

* * * * *